United States Patent [19]

Ilizarov et al.

[11] Patent Number: 4,615,338
[45] Date of Patent: Oct. 7, 1986

[54] AUTOMATIC COMPRESSION-DISTRACTION APPARATUS

[75] Inventors: Gavriil A. Ilizarov; Alexandr P. Predein; Vyacheslav M. Bykov, all of Kurgan, U.S.S.R.

[73] Assignee: Kurgansky Nauchno-Issledovatelsky Institut Experimentalnoi I Klinicheskoi Ortopedii I Travmatologii, Kurgan, U.S.S.R.

[21] Appl. No.: 777,425

[22] Filed: Sep. 18, 1985

[51] Int. Cl.[4] ............................................. A61F 5/04
[52] U.S. Cl. ............................... 128/92 A; 128/92 G
[58] Field of Search ................ 128/92 A, 92 G, 92 R

[56] References Cited

U.S. PATENT DOCUMENTS

| 2,055,024 | 9/1936 | Bittner, Jr. | 128/92 A |
| 4,157,715 | 6/1979 | Westerchoff | 128/92 G |
| 4,502,473 | 3/1985 | Harris et al. | 128/92 A |
| 4,573,459 | 3/1986 | Litton | 128/92 A |

FOREIGN PATENT DOCUMENTS

| 848011 | 7/1981 | U.S.S.R. | |
| 865284 | 9/1981 | U.S.S.R. | |
| 986404 | 1/1983 | U.S.S.R. | 128/92 A |

Primary Examiner—Robert Peshock
Assistant Examiner—C. W. Shedd
Attorney, Agent, or Firm—Fleit, Jacobson, Cohn & Price

[57] ABSTRACT

A drive of a compression-distraction apparatus, comprising a lead screw whose thread is mated with an opening of a ratchet wheel placed in a housing, a pawl interacting with teeth of the wheel and connected to a load-bearing element manufactured from an alloy possessing plastic memory. The load-bearing element has a rectilinear shape and is essentially a tie-rod whose one end is rigidly secured to the housing while the other end is coupled to a resilient member and the pawl, said load-bearing element being further provided with an electric heater connected to the housing.

10 Claims, 12 Drawing Figures

AUTOMATIC COMPRESSION-DISTRACTION APPARATUS

FIELD OF THE INVENTION

The present invention relates to medical equipment employed in orthopedics and traumatology for treating various congenital and acquired shortenings and other defects or skeletal segments and, more particularly, it relates to drives of compression-distraction apparatuses.

BACKGROUND OF THE INVENTION

There is known in the art a drive of a compression-distraction apparatus (cf., U.S.S.R. Inventor's Certificate No. 848,011, cl. A 61 B 17/18, published in the Bulletin of Inventions, No. 27, 1981), comprising a lead screw, a gear mounted thereon and, series-connected with said gear via reduction gear, a ratchet wheel, a lever with a pawl and an electromagnet interacting with one of the lever arms. Said prior art device is further provided with a power pack connected to an electromagnet.

The afore-described drive provides for measured and atraumatic micromovement of bone fragments. However, said prior art drive suffers from excessively large mass and dimensions whereby its clinical use is rather difficult.

This disadvantage is primarily due to the low specific force per unit weight developed by the drive.

Another prior art drive of a compression-distraction apparatus appears more improved (cf., U.S.S.R. Inventor's Certificate No. 865,284, cl. A 61 B 17/18, published in the Bulletin of Inventions, No. 35, 1981) and provides, analogously with the foregoing prior art drive, for atraumatic movement of bone fragments that is close to natural physiological growth. Said latter prior art drive of compression-distraction apparatus comprises a lead screw mated by threading with an opening of a ratchet wheel rotatably positioned in a housing. Interacting with teeth of the ratchet wheel is a pawl coupled with a load-bearing element manufactured from an alloy possessing plastic memory and having an electric heater. The ratchet wheel of said prior art drive has internal mesh while the pawl is positioned on the smaller arm of a lever arranged inside the wheel and lying in the same plane therewith. The load-bearing element is fashioned as a shackle arranged below the lever in a parallel plane therewith and connected by its one end with the housing wall while its other end is connected with the long arm of the lever and with a resilient member serving to keep the load-bearing element in a bent position. The electric heater with which the load-bearing element is provided is connected to a power pack.

The last-described prior art unit, while exhibiting the same distraction force as the previously described electromagnetic drive, features considerably smaller dimensions and weight. However, attempts at expanding the range of clinical application of said latter unit have shown that the force it develops is insufficient for ensuring reliable operation. Thus, an increase of the distraction force above 300-350 N leads to failures in the drive operation caused by the fact that the load-bearing element reaches the breaking stress. Actual loads in the course of the drive operation may exceed considerably those cited above in view of the functional load on an extremity reaching, as a maximum, the magnitude of the patient's weight. Therefore, it is very important to find a solution to the problem of ensuring an adequate distraction force.

The distraction force developed by the prior art drive may be increased by way of increasing the cross-sectional area and dimensions of the load-bearing element. However, an increase of thos dimensions results in an increase of the ratchet wheel diameter, housing diameter and of the overall weight of the drive. Second, an increase of the cross-sectional area and dimensions of the load-bearing element involves a direct increase in the consumption of energy required for heating the element to the operation temperature, which affects considerably the duration of autonomous supply of the drive.

Therefore, the prior art drive may only develop a distraction force required for its clinical use only on condition of a considerable increase of the drive dimensions and weight. This restricts considerably the range of clinical application of the unit and, in a number of cases, e.g., in apparatuses for elongation of short tubular bones (phalanges, metacarpal bones), makes it problematic. Moreover, a rise in the energy intensity of the drive resulting from an increase of the cross-sectional area and dimensions of the load-bearing element reduces the autonomous supply of the drive and further restricts the range of clinical application of the prior art unit.

SUMMARY OF THE INVENTION

It is an object of the present invention to develop a drive of a compression-distraction apparatus that would provide a distraction force sufficient in all clinical cases while featuring the minimum energy intensity, dimensions and mass.

Said and other objects of the present invention are attained owing to the fact that in a drive of a compression-distraction apparatus, comprising a lead screw mated with a ratchet wheel placed in a housing, and a pawl interacting with teeth of said wheel and connected to a load-bearing element manufactured from an alloy possessing plastic memory, said load-bearing element having an electric heater, connected to the housing and interacting with a resilient member, according to the present invention, the load-bearing element has a rectiliner shape and is essentially a tie-rod whose one end is rigidly secured to the housing while its other end is coupled to the resilient member and the pawl.

Such an arrangement of the drive of the invention provides for the maximum distraction force under conditions of the minimum energy intensity, dimensions, weight and structural complexity of the drive.

It is expedient that the resilient member coupled with the load-bearing element be likewise manufactured from a material possessing plastic memory and featuring the temperature of inverse martensite transformation of about 100°-150° C. below that of the material of the load-bearing element.

This helps reduce the resistance to the working stroke of the mechanism.

With a view to simplifying the structure, it is expedient that the tie-rod be fashioned as a wire.

In order to reduce the heat losses upon heating the tie-rod, it is expedient that it should be fashioned as a thin-walled hollow tube with the electric heater accommodated thereinside.

It is further expedient that the pawl be fashioned as a resilient clamp whose ends are rigidly connected to the tie-rod while the middle portion of said clamp interacts with a tooth of the ratchet wheel.

This helps simplify the structure and make it more miniature.

It is sound practice to connect one end of the tie-rod to the housing by means of an adjusting member, this enabling one to set the best position of the pawl connected with the other end of the tie-rod irrespective of possible deviations from its length.

In addition, it appears beneficial in a number of cases to couple the other end of the tie-rod to the pawl by means of a lever whose smaller arm is connected with the tie-rod. This will help reduce the tie-rod length required for the working stroke, as well as the consumption of energy required for heating the tie-rod.

While so doing, it is advisable that the lever and tie-rod be positioned in a plane normal to the plane of the ratchet wheel. This results in a smaller transverse dimension of the housing.

In other cases, it appears more important to reduce the housing dimension along the lead screw axis. To this end, in the housing there is provided a channel designed to accommodate the tie-rod and positioned tangentially to the ratchet wheel which has external mesh while the resilient member is essentially a helical spring positioned in the same channel, with the tie-rod being placed inside the helical spring coaxially therewith and secured by its one end in an end wall of the channel while the helical spring is compressed between said wall and a washer connecting the other end of the tie-rod with the pawl.

For some applications of the drive of the invention, it is expedient that the lead screw be provided with a longitudinal flat interacting with a lock screw which is immovable relative to the housing. This enables one to use the herein disclosed drive in compression-distraction apparatuses of diverse designs, i.e., improves its universality.

BRIEF DESCRIPTION OF DRAWINGS

The present invention will be more apparent upon considering the following detailed description of exemplary embodiments of the herein disclosed drive of a compression-distraction apparatus, with due reference to the accompanying drawings in which.

DESCRIPTION OF PREFERRED EMBODIMENTS OF INVENTION

Figures 1, 2, 3, 4:
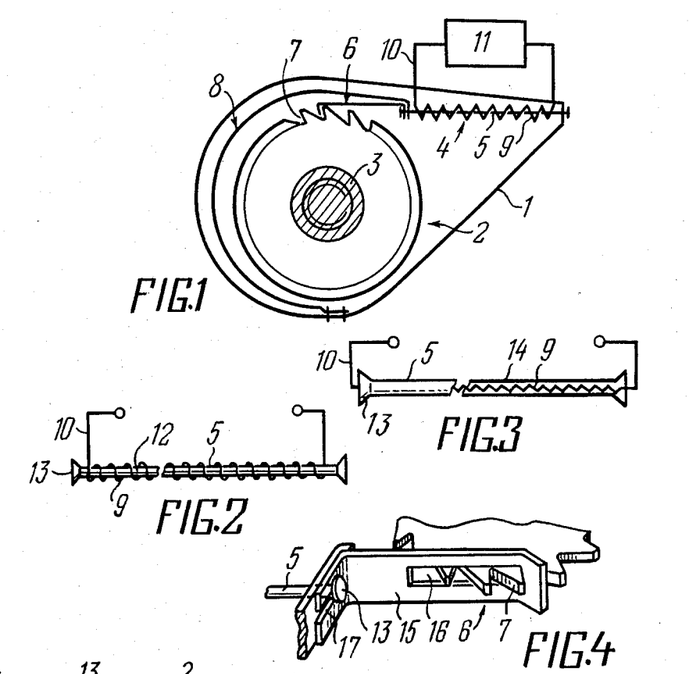
FIG. 1 is a diagrammatic view of the drive according to the present invention.
FIG. 2 shows an embodiment of the load-bearing element, according to the present invention.
FIG. 3 shows another embodiment of the load-bearing element, according to the present invention.
FIGS. 4, 5, 6 illustrate embodiments of the pawl of the ratchet mechanism, according to the present invention.

Referring now to FIG. 1 of the accompanying drawings, the herein disclosed drive of a compression-distraction apparatus comprises a housing 1 rigidly mounted on one of the apparatus supports (not shown in the drawing) with a ratchet wheel 2 positioned in said housing 1 with a possibility of performing rotation. An axial opening of the ratchet wheel 2 is provided with screw thread with which there is movably mated a lead screw 3 rigidly attached to another support of the compression-distraction apparatus connected with the bone fragment being moved (not shown in the drawing). The drive is provided with a load-bearing element 4 which has a rectilinear shape and is fashioned as a tie-rod 5 whose one end is rigidly attached to the housing 1 while its other end is rigidly connected with a pawl 6 resiliently biased against a toothed rim of the ratchet wheel 2 and meshing by its end with one of ratchet wheel teeth 7. The end of the tie-rod 5 coupled with the pawl 6 is also connected with a resilient member 8 maintaining the tie-rod 5 in a permanently stretched out state. The tie-rod 5 is provided with an electric heater 9 which is electrically connected (shown at 10) with a power pack 11 which may be switched both manually and automatically with the aid of a special control unit (not shown in the drawing).

The load-bearing element 4 (5) is manufactured from a known alloy, say, of nickel and titanium possessing the so-called plastic memory (or thermomechanical recovery effect as it is also called). This effect is characterized by the fact that an alloy capable of exhibiting it has, at a temperature below the point of direct martensite transformation (phase variation of the alloy structure), a modulus of elasticity which is considerably less than that at a temperature above the point of inverse martensite transformation. Therefore, a body manufactured from such an alloy, subjected to cold plastic deformation and then heated to a temperature above that specified hereinbefore tends to recover the original (prior to deformation) shape and dimensions and, in so doing, may develop rather considerable mechanical stresses owing to the afore-mentioned difference between the moduli of elasticity in the cold and hot states.

The resilient member 8 may likewise be manufactured from an alloy possessing plastic memory, however, featuring the temperature of inverse martensite transformation of about 100°-150° C. below that of the material of the load-bearing material 4. In this case, the material of the resilient member 8 at the operating temperature of the drive is in the superelastic state characterized by a very flat curve. This provides for a lower resistance to the working stroke as compared with the embodiment in which the resilient member 8 is made of steel used for manufacturing springs.

The tie-rod 5 may be manufactured from strip, wire, band, sheet material and material of other shapes. In particular, one tie-rod embodiment shown in FIG. 2 provides for the manufacture of the tie-rod 5 from a piece of wire 12 with thickenings 13 at the ends for rigidly securing the tie-rod in mated parts of the drive (not shown in the drawing).

The electric heater 9 is in thi case fashioned as a coil of thin wire featuring a high ohmic resistance and insulated from the tie-rod 5 by a thin thermostable dielectric film (not shown in the drawing). On the outside, the electric heater 9 is covered with heat insulation made of, say, glass fiber (not shown in the drawing).

The afore-described embodiment of the tie-rod 5 is the simplest one and most adaptable to streamlined production methods.

Another embodiment of the tie-rod 5 shown in FIG. 3 is that in the form of a hollow tube 14 accommodating thereinside the electric heater 9 electrically insulated from the tube surface (insulation not shown). The ends of the hollow tube 14 may have thickenings 13 analogous with those described above, which can be made both by expanding the tube ends and by upsetting. This embodiment of the load-bearing element helps considerably reduce the heat losses and, as a result, additionally increase the autonomous supply capabilities of the herein disclosed device.

The pawl 6 interacting with the teeth 7 of the ratchet wheel 2 may also have various embodiments. The most advantageous embodiments fo the pawl in the herein disclosed drive are those wherein the possibility of permanent contact of the pawl with the teeth of the ratchet wheel 2 is ensured thanks to the intrinsic elasticity of the pawl 6. This provides for smaller dimensions and lesser complexity of the drive as compared with other possible embodiments of the pawl wherein it is, say, rigid and provided with an axle and a separate resilient member for urging it against the ratchet wheel 2 (said latter embodiments are not shown in the drawing).

The resilient pawl 6 may be fashioned, in particular, as a plane plate 15 shown in FIG. 4 having at its end a slot 16 for engagement with the teeth 7 of the ratchet wheel 2. Provided at the othere end of the plate 15, bent at right angles, is a slot 17 forming a seat for joining the pawl 6 with the thickening 13 formed at the end of the tie-rod 5(4). The end of the resilient member 8 maintaining the tie-rod 5 in a tensioned state locks the thickening 13 at its end in the slot 17.

Figure 5:
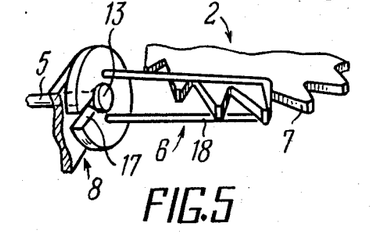
Figure 6:
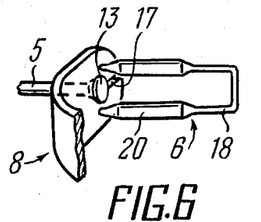

According to another embodiment shown in FIG. 5, the resilient pawl 6 is fashioned as a wire clamp. Its ends have a length sufficient for ensuring desired elasticity and are rigidly secured in a washer 19 which has a slot 17 analogous to that described above and forming a seat to accommodate the thickening 13 at the end of the tie-rod 5. In the case illustrated in FIG. 6, when the resilient member 8 is made plane, the ends of the clamp 18 may be attached directly to its end also having a slot 17 for securing the thickening 13 of the tie-rod 5. In order to reduce the rigidity of the clamp 18, it is expedient that the clamp be flattened over a portion 20 adjoining the termination point (cf., FIG. 6).

Figure 7:
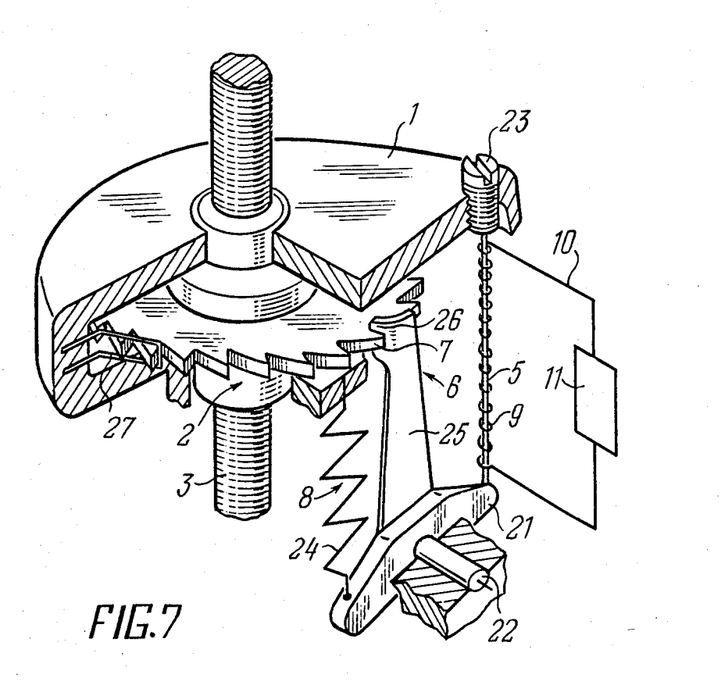
FIG. 7 shows diagrammatically an embodiment of the drive according to the present invention.

In some cases, as shown in FIG. 7, it is advisable that an end of the tie-rod 5 be coupled with the pawl 6 by means of a lever 21 mounted in the housing 1 on an axle 22. While so doing, the smaller arm of the lever 21 is coupled with the tie-rod 5 thereby reducing the length of the tie-rod 5 necessary to provide for the working stroke and, consequently, the dimensions of the housing 1 and the consumption of energy required for heating the tie-rod 5. Further, the lever 21 and tie-rod 5 may be positioned in a plane normal to the axis of the ratchet wheel 2 to provide for a reduction of transverse dimenion of the housing 1 of the drive. The end of the tie-rod 5 connected with the housing 1 may be coupled therewith by means of an adjusting member 23 fashioned as, say, a screw positioned in the housing coaxially with the tie-rod 5 and having in its body a seat (not shown in the drawing) for securing therein the end of the latter. The resilient member 8 may in this case be fashioned as a tension spring 24 coupled with the lever 21 and tending to turn the latter in a direction ensuring the tensioning of the tie-rod 5.

According to this embodiment of the drive, the pawl 6 may be fashioned as a resilient plate 25 positioned in the plane of rotation of the lever 21 and presenting its bigger arm. The plate 25 has at its end a bend 26 meshing with the teeth 7 of the ratchet wheel 2. In order to preclude reverse rotation of the ratchet wheel 2 upon idle stroke of the pawl 6, the drive may be provided with an additional pawl 27 made as, say, a resilient wire clamp analogous with that described above. While so doing, the pawl 27 is immovably mounted on the housing 1. The need for such a pawl may arise upon no-load operation of the mechanism when the friction of the pawl 25 against the back edge of the tooth 7 of the ratchet wheel 2 may exceed the friction of the latter wheel mating with the housing 1 and lead screw 3.

For quite a few applications of the drive of the invention, for instance, those shown in FIGS. 8, 9, 10, 11 and 12, one may find more expedient its plane arrangement when the tie-rod 5 is positioned in the same plane with the ratched wheel 2. Such an arrangement leads to a considerable reduction of the axial dimension of the housing 1, i.e., its dimension along the axis of the lead screw 3, as well as renders the housing 1 less bulky, and permits of its use is most diverse compression-distraction apparatuses.

Figure 8:
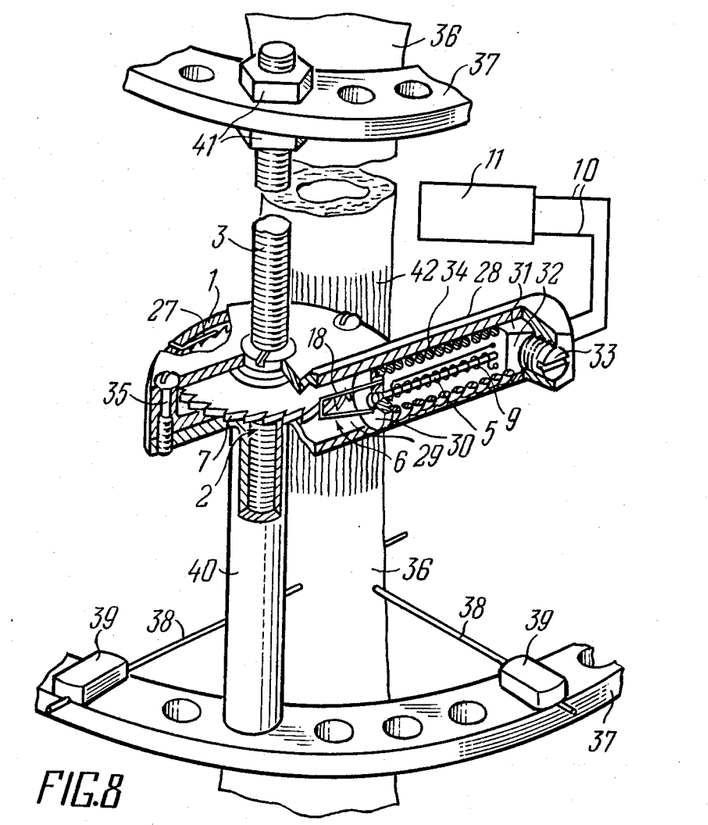
FIG. 8 shows another embodiment of the drive according to the present invention (in section), mounted in a prior art compression-distraction apparatus for bone elongation.

Consider now FIG. 8 which shows, in section, the aforementioned embodiment of the drive mounted in a prior art compression-distraction apparatus for bone elongation. The ratchet wheel 2 with external mesh is rotatably mounted in a housing 1 having a connection pipe 28 forming a channel 29 designed to accommodate the tie-rod 5. The channel 29 and the tie-rod 5 coaxial therewith are arranged tangentially to the ratchet wheel 5. The tie-rod 5 by its one end is rigidly attached to a washer 30 mounting a resilient pawl 6 fashioned as the afore-described wire clamp 18 and engaged with one of the teeth 7 of the ratchet wheel 2. The washer 30 is movably mated with the channel 29. The other end of the tie-rod 5 is rigidly secured in an adjusting member 31 fashioned as a cylindrical stopper arranged at the channel end. Said stopper has a V-shaped flat 32 interacting with the end face of a lock screw 33 positioned in the immediate vicinity thereof in a thickened wall of the pipe 28. Positioned between the end face of the adjusting member 31 and the washer 30 in a resilient member fashioned as a compression spring 34 maintaining the tie-rod 5 in a tensioned state. The spring 34, same as the washer 30, is movably mated with the wall of the channel 29. Interacting with the teeth 7 of the ratchet wheel 2 is the additional pawl 27 serving to preclude reverse rotation of the ratchet wheel 2. The electric heater 9 is fashioned as described above and is likewise electrically connected with the power pack 11. The housing 1 of the drive is provided with screws 35 for its fastening in the compression-distraction apparatus.

In particular, the herein disclosed drive may be mounted in an apparatus for the elongation of a bone 36. Said apparatus is conventionally shown in FIG. 8 as portions of ring- or arc-shaped supports 37 carrying pins 38 passed through the bone 36, tensioned on said supports and attached thereto by means of grips 39. Rigidly mounted on one of the supports 37, say, the bottom one, are tubular pillars 40 (one of said pillars shown in the drawing). The housing 1 of the drive is rigidly attached to the top portion of the pillar 40 by means of the screws 35. The lead screw 3 passing through the housing 1 is in part accommodated within the tubular pillar 40. The other end of the lead screw, positioned outside of the pillar 40 and housing 1, is rigidly attached by nuts 41 to the top support 37 of the compression-distraction apparatus, which is analogously connected by means of pins (not shown in the drawing) with the proximal portion of the bone 36. Bone regenerate 42 between the proximal and distal portions of the bone 36 binds them together.

In another apparatus (cf., FIG. 9) designed for compensating total defect of the bone 36 by bringing down its fragment 43, provision is made of analogous supports 37 rigidly connected by means of the pins 38 to the distal and proximal portions of the bone 36 featuring extensive defect in its middle portion. The supports 37 are rigidly coupled with each other by means of threaded rods 44. Mounted on the opposite sides of the distal support 37 with the aid of brackets 45 and platforms 47 articulated with the latter by an axle 46 are drives whose housings 1 are rigidly attached to said platforms 47 by the screws 35.

Figures 9, 10:
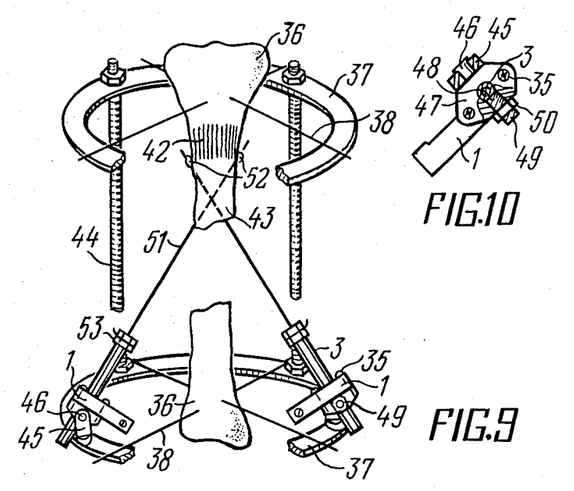
FIG. 9 illustrates an application of the drive according to the present invention in a prior art apparatus for compensating total bone defect.
FIG. 10 is a section taken along the axis of the pivoted platform mounting the housing of the drive according to the present invention.

The lead screw 3 of each drive has a plane longitudinal flat 48 and is passed through an opening in the platform 47 which is normal to the axle 46. The plane flat 48 interacts with the end face of a lock screw 49 thereby preventing the lead screw 3 from rotating about its axis. The screw 49 may be positioned in the drive housing 1 as well, however, it is most practical to position it in a part immovably mated with the housing 1, in particular, in the platform 47. The screw 49 is provided with a lock nut 50 fixing it in position.

Passed via bone fragment 43, severed from the proximal portion of the bone 36 and bound to the latter by the subsequently formed bone regenerate 42, are pins 51 having at their ends thickenings 52 located on the outside of the bone fragment 43. The pins 51 are passed in the direction of the axes of the lead screws 3 positioned on the bone side external with respect to the thickenings 52 and are rigidly secured to the ends of said screws by nuts 53.

Figure 11:
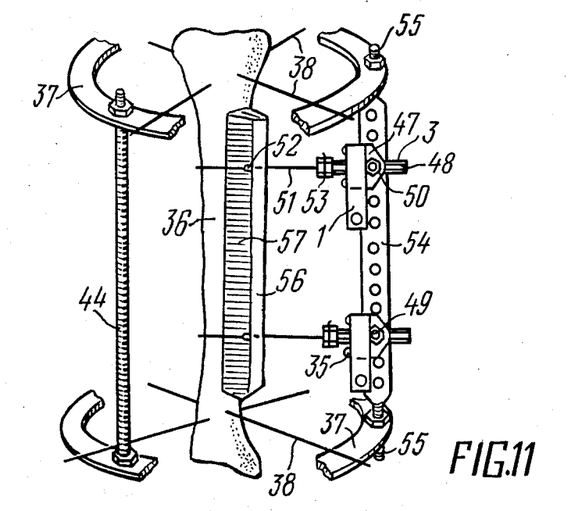
FIG. 11 illustrates an application of the drive according to the invention in a prior art apparatus for bone expansion.

According to yet another embodiment of the apparatus shown in FIG. 11 and designed for the expansion of the bone 36, as distinct from the foregoing, the drives are mounted with the aid of the platforms 47 on a rigid beam 54 whose ends are rigidly attached to the supports 37 with the aid of threaded shanks 55. The lead screws are positioned transversely to the axis of the bone 36 and are connected, by means of analogous pins 51 having thickenings 52 at their ends, with a fragment 56 longitudinally chipped off the bone 36 and connected therewith by bone regenerate 57.

Figure 12:
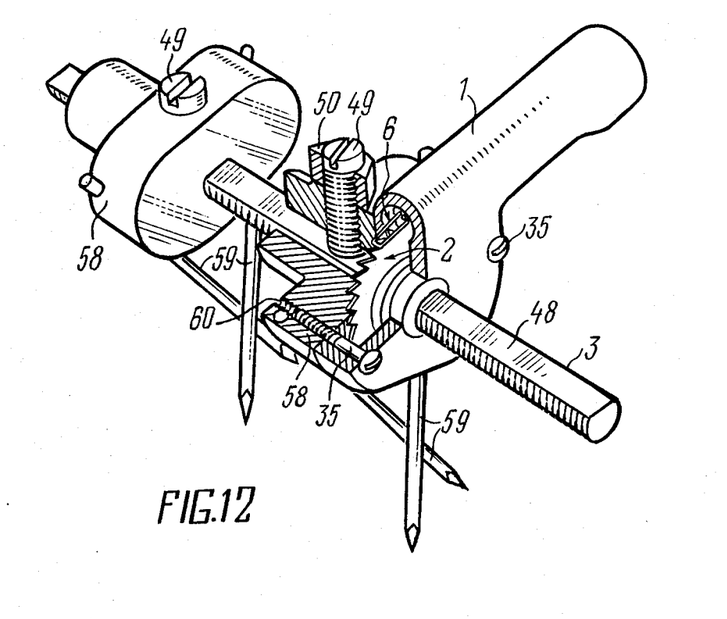
FIG. 12 illustrates an application of the drive according to the present invention in a prior art apparatus for elongation of short tubular bones such as stumps of phalanges, metacarpal bones etc.

And finally described herein is the application of the drive of the invention in a prior art apparatus for the elongation of short tubular bones, illustrated in FIG. 12. This apparatus is used when the anatomical position of bones such as phalanges or metacarpal bones makes difficult or prohibits the through passage of pins as shown in the preceding drawings.

In the prior art apparatus for the elongation of short tubular bones use is made of a drive with the lead screw 3 having the longitudinal plane flat 48. The apparatus consists essentially of nail holders 58 wherein there are cantilever-mounted nails 59 crossing in the plane of bone fragments (not shown in the drawing). The nail holders 58 are coupled with each other by means of the lead screw 3 with the flat 48, which is positioned in smooth openings formed in said nail holders and normal to the plane of positioning of the nails 59. The nail holders 58 are further provided with the lock screws 49 interacting by their end faces with the flat 48 for precluding their rotation about the axis of the lead screw 3. One of the nail holders 58 is positioned at the end of the lead screw 3 and is rigidly secured thereon by means of the screw 49. Another nail holder 58 is positioned on the lead screw 3 for translational movement therealong, which is attained by adjustment of the screw 49 which provides for the minimum gap required for displacement in mating with the flat 48.

The position of the screw 49 attained as a result of adjustment is fixed by the lock nut 50. The movable holder 58 has threaded holes 60 accommodating the screws 35 serving to rigidly attach the housing 1 of the drive to said holder.

The electric connection 10 and the power pack 11 are not shown in FIGS. 9, 10, 11 and 12 of the drawings.

The herein disclosed drive of a compression-distraction apparatus operates in the following manner.

A current pulse is fed from the power pack 11 via wires 10 to the electric heater 9, the duration of said pulse being sufficient for heating the tie-rod 5 to a temperature at which inverse martensite transformation occurs. The modulus of elasticity of the material of the tie-rod 5 increases considerably and the tie-rod reduces in length while overcoming the forces of friction in the mechanism and the resistance of the resilient member 8. In so doing, the tie-rod 5 displaces the pawl 6 which comes by its one end against one of the teeth 7 of the ratchet wheel 2 and performs the working stroke to turn said wheel around the axis of the lead screw 3. The latter is incapable of rotation and starts moving along its axis to displace the support of the compression-distraction apparatus together with the bone fragment rigidly connected therewith (not shown in the drawing). The working stroke of the pawl 6 continues until the load-bearing element 4 (tie-rod 5) is reduced to the size it had prior to the application of tensile stress from the resilient member 8. The length of the load-bearing element 4 (tie-rod 5) is selected sufficient for moving its end coupled with the pawl 6 through a value a defined by the inequality $t < a < 2t$ wherein t is the pitch of the teeth 7 of the ratchet wheel 2.

After the supply to the electric heater 9 is switched off, the load-bearing element 4 (tie-rod 5) starts cooling down. While so doing, at a temperature below that of direct martensite transformation, the modulus of elasticity of its material decreases considerably. As a result, the resilient member 8 stretches the load-bearing element 4 (tie-rod 5) to the dimension it had before heating. In the course of elongation of the load-bearing element 4(5), the pawl 6 performs the idle stroke to advance by its end upon the sloping back edge of the tooth 7 and, in so doing, to resiliently bend back. At the end of the idle stroke, the end of the pawl 6 comes to be engaged with the subsequent tooth 7. The ratchet wheel 2 stays motionless in the course of the idle stroke because the forces of friction due to its mating with the housing 1 and screw 3 prove incommensurably greater than the force of friction of the end of the pawl 6 against the back edge of the tooth 7.

Upon supply of subsequent pulse of current from the power pack 11 to the electric heater 9, the afore-described process is repeated. Therefore, the operation of the drive takes place under conditions of alternating heating and cooling of the load-bearing element 4 (tie-rod 5). The rate of axial displacement of the lead screw 3 depends upon the repetition rate of the pulses of current supplying the electric heater 9, which may be preset depending upon specific biological conditions determining whether such rate of displacement is the optimum one. The drive may be controlled automatically using a special control unit which does not fall within the scope of the present patent application.

The operation of the drive embodiment illustrated in FIG. 7 is generally analogous with that described above, however, with some distinctions. In particular, upon alternating heating and cooling of the tie-rod 5, the pawl 6 performs rotary reciprocation about the axle 22 of the lever 21. The latter turns counterclockwise upon the reduction of the tie-rod 5 being heated and clockwise upon its cooling down, under the effect of the tension spring 24 coupled with the lever 21. When the lever 21 turns counterclockwise, the working stroke occurs as a result of which the bent out end 26 of the pawl 6 comes against the tooth 7 of the ratchet wheel 2 to turn the latter and cause axial displacement of the lead screw 3 which is incapable of rotation due to its rigid attachment to the support of the compression-distraction apparatus (not shown in the drawing). In the course of the working stroke, the additional pawl 27 enables the wheel 2 to turn, by coming upon the sloping back edge of the tooth 7 while bending out resiliently. At the end of the working stroke, said additional pawl gets in the subsequent gap between the teeth 7. Upon the turning of the lever 21 in the opposite direction which starts as a result of tension of the cooling down tie-rod 5 by the spring 24, there occurs the idle stroke of the pawl 6 which comes upon the sloping back edge of the subsequent tooth 7 while bending out resiliently. the pawl 27 which at this moment engages one of the teeth 7 of the ratchet wheel 2 precludes a reverse turn of the latter which might occur due to the force of friction of the pawl 6 against the back edge of the tooth 7. The relative position of the pawls 27 and 6 is adjusted with the aid of the adjusting member fashioned as, say, screw 23. Axial displacement of said screw 23 causes the lever 21 to turn and the pawl 6 to change its position relative to the pawl 27 rigidly attached to the housing 1.

The drive embodiment shown in section in FIG. 8 generally operates analogously with that described above. Some distinctions are due to differences in the structural embodiment of the drive.

In particular, as distinct from rotary reciprocation of the pawl 6 according to the afore-described embodiment, in this latter embodiment the pawl performs reciprocating motion along the axis of the channel 29. Upon heating, the tie-rod 5 decreases in length to compress the spring 34 and to provide for the working stroke of the pawl 6 mounted on the washer 30 movable along the axis of the channel 29. Upon cooling down, the tie-rod 5 is stretched by the spring 34 to provide for the working stroke of the pawl 6. The additional pawl 27 operates analogously with that described in connection with the foregoing embodiment.

The relative position of the pawls 6 and 27 is adjusted by unscrewing the screw 33 which releases the adjusting member fashioned as stopper 31 and by moving same along the axis of the channel 29. After that, the attained position is secured by means of the same screw 33 resting against the V-shaped flat 32 which ensures the reliability of fastening.

In the course of the drive operation the lead screws 3 move synchronously along their axis to cause relative movement of the proximal and distal supports 37 and of the like portions of the bone 36 connected therewith, this resulting in the traction of the bone regenerate 42 joining said portions to each other.

When compensating total bone defect, as shown in FIG. 9, axial movement of the lead screws 3 causes the movement of the bone fragment 43 connected therewith by means of pins 51 and gradual traction of the bone regenerate 42. As the bone fragment 43 moves, the housings 1 of the drives mounted on the articulated platforms 47 move until the fragment being displaced comes against the bottom portion of the bone 36. Thereupon, their joint is knitted in a conventional manner.

In the drive embodiment illustrated in FIG. 11, the movement of the fragment 56 longitudinally chipped off the bone 36 and connected therewith by the bone regenerate 57 is performed analogously. The only difference is that the bone fragment 56 is moved under the effect of the screws 3 in the transverse direction until the cross-section of the bone 36 being expanded becomes sufficient. After that, the movement of the fragment 56 is discontinued and the fragment is stabilized by one of the conventional techniques until the bone regenerate 57 is fully changed to bone tissue.

In the drive embodiment illustrated in FIG. 12, the rotation of the ratchet wheel 2 causes translation motion of the housing 1 and of the nail holder 58 rigidly connected therewith along the axis of the lead screw 3 relative to another nail holder 58 rigidly attached to the cone of the former nail holder. In so doing, there occurs displacement of bone fragments (not shown in the drawing) rigidly connected to the nail holders 58 by the nails 59, as well as the elongation of bone at the expense of growing regenerate joining together said bone fragments.

Surgical techniques associated with osteotomy, drawing of pins and nails through live tissue, as well as with the assembly of compression-distraction apparatuses, follow universally known procedures and are not described in the instant application.

The herein disclosed structure, as distinct from prior art ones, results in a drive capable of exhibiting sufficient force and having dimensions which are so small as to allow of its use for the elongation of short stumps of phalanges and metacarpal bones of the hand wherein desired relative values of bone elongation reach 100% and more. Given such elongation values, the efficiency of the herein disclosed drive is especially high.

The afore-mentioned possibility is primarily due to the fact that the adequate simplicity of design permits of making the drive miniature while high specific forces developed by the load-bearing element of the drive provide for the margin of distraction force sufficient for reliable operation of the drive.

Apart from the reliability in operation, the simplicity of design leads to low manufacturing costs and, consequently, to universal utilization of the herein disclosed drive.

It should be further noted that, along with the use of the drive of the invention for treatment, it is expedient to use the drive in experimental studies into biological regularities of regeneration of tissues. The small weight and dimensions of the drive render it advantageous over prior art inasmuch as it facilitates the use of smaller animals for experimental purposes, which reduces the cost of studies and, at the same time, provides a higher degree of uniformity of the starting biological material thereby improving the reliability of obtained results.

What is claimed is:

1. A surgical orthopedic apparatus, comprising:
    support members;
    pillars serving to connect the support members;
    pins passing through bone and attached to said support members;
    a drive designed to adjust the relative position of said support members, said drive including:
    a housing secured on said pillars;
    a lead screw mounted in a pillar and connected by its one end to said support member;
    a ratchet wheel mounted in said housing and interacting with said lead screw;
    a pawl connected with teeth of said ratchet wheel;
    a load-bearing element coupled by its one end to said pawl while its other end is rigidly attached to said housing; said load-bearing element being essentially a tie-rod manufactured from an alloy possessing plastic memory;
    a resilient member fashioned as a spring with its one end attached to said housing and the other end interacting with said load-bearing element;
    an adjusting member arranged in said housing, connected by its one end to said tie-rod and designed for setting the force of tensioning said tie-rod.

2. An apparatus as claimed in claim 1, wherein said resilient member is manufactured from an alloy possessing plastic memory and featuring the temperature of inverse martensite transformation of about 100°–150° C. below that of the material of the load-bearing element.

3. An apparatus as claimed in claim 1, wherein said tie-rod is fashioned as a thin-walled tube while the electric heater is positioned thereinside.

4. An apparatus as claimed in claim 1, wherein said tie-rod is fashioned as a wire.

5. A surgical orthopedic apparatus, comprising:
    support members;
    pillars serving to connect said support members;
    pins passing through bone and attached to said support members;
    at least one pin passing through a fragment chipped off the bone and attached to a lead screw designed to adjust the position of the said pin;
    a drive designed to adjust the relative position of said pin and said bone fragment, attached to said support member and including:
    a housing mounted on at least one said support member;
    a ratchet wheel mounted in said housing and interacting with said lead screw;
    a pawl connected with teeth of said ratchet wheel;
    a load-bearing element coupled by its one end to said pawl and by its other end to said housing, said load-bearing element being essentially a tie-rod manufactured from an alloy possessing plastic memory;
    a resilient member fashioned as a spring with its one end attached to said housing and the other end interacting with said load-bearing element;
    an electric heater mounted in said housing and interacting with said load-bearing element;
    an adjusting member arranged in said housing, connected by its one end to said tie-rod and designed for setting the force of tensioning said tie-rod.

6. An apparatus as claimed in claim 5, wherein said pawl is fashioned as a resilient clamp whose end is rigidly attached to said tie-rod while the middle portion of said clamp interacts with teeth of said ratchet wheel.

7. An apparatus as claimed in claim 5, wherein said tie-rod is coupled by its one end to said pawl by means of a lever having a bigger arm and a smaller arm, the smaller arm of said layer being connected to said tie-rod.

8. An apparatus as claimed in claim 5, wherein said lever and said tie-rod are positioned in a plane normal to the plane of said ratchet wheel.

9. A surgical orthopedic apparatus, comprising:
    support members;
    at least one lead screw designed to adjust the relative position of said support members;
    pins passing through bone and attached to said support members;
    a drive designed to adjust the relative position of the support members and attached to one of the latter, said drive including:
    a housing mounted on at least one of said support members;
    a ratchet wheel mounted in said housing and interacting with said lead screw;
    a pawl connected with teeth of said ratchet wheel;
    a load-bearing element coupled by its one end to said pawl and by its other end to said housing, said load-bearing element being essentially a tie-rod manufactured from an alloy possessing plastic memory;
    a resilient member fashioned as a spring comopressed within said housing between one of end walls thereof and said pawl, with said tie-rod being positioned inside said spring coaxially therewith;
    an electric heater mounted in said housing and interacting with said tie-rod;
    an adjusting member arranged in said housing and designed for setting the force of tensioning said tie-rod and said spring.

10. An apparatus as claimed in claim 9, wherein said lead screw is provided with a longitudinal flat and with a lock screw mounted immovably relative to said housing.

* * * * *